(12) United States Patent
Wu

(10) Patent No.: US 11,299,748 B2
(45) Date of Patent: Apr. 12, 2022

(54) KIT FOR CONSTRUCTING TRANSPOSON AND USE THEREOF

(71) Applicant: GenomeFrontier Therapeutics, INC., Grand Cayman (GB)

(72) Inventor: Sareina Chiung-Yuan Wu, Taipei (TW)

( * ) Notice: Subject to any disclaimer, the term of this patent is extended or adjusted under 35 U.S.C. 154(b) by 739 days.

(21) Appl. No.: 16/073,343

(22) PCT Filed: Mar. 25, 2016

(86) PCT No.: PCT/CN2016/077323
§ 371 (c)(1),
(2) Date: Jul. 27, 2018

(87) PCT Pub. No.: WO2017/161553
PCT Pub. Date: Sep. 28, 2017

(65) Prior Publication Data
US 2019/0040414 A1     Feb. 7, 2019

(51) Int. Cl.
*C12N 15/85*     (2006.01)
*C12N 9/12*     (2006.01)

(52) U.S. Cl.
CPC ........... *C12N 15/85* (2013.01); *C12N 9/1241* (2013.01); *C12Y 207/07* (2013.01); *C12N 2800/90* (2013.01)

(58) Field of Classification Search
None
See application file for complete search history.

(56) References Cited

U.S. PATENT DOCUMENTS

2015/0283267 A1* 10/2015 Vandendriessche ... C12N 15/86
514/44 R

OTHER PUBLICATIONS

Alignment of SEQ ID No. 29 from US Patent Application Publication No. 20150283267 with SEQ ID No. 3. Search conducted on Jul. 4, 2021. 1 page. (Year: 2021).*
Alignment of SEQ ID No. 30 from US Patent Application Publication No. 20150283267 with SEQ ID No. 4. Search conducted on Jul. 4, 2021. 1 page. (Year: 2021).*
Alignment of BEI78535 with SEQ ID No. 5'. Search conducted on Jul. 4, 2021. 2 pages. (Year: 2021).*
Alignment of BFC33626 with SEQ ID No. 5. Search conducted on Jul. 4, 2021. 2 pages. (Year: 2021).*
Alignment of BEI78537 with SEQ ID No. 5. Search conducted on Jul. 4, 2021. 2 pages. (Year: 2021).*
Alignment of BFC33628 with SEQ ID No. 5. Search conducted on Jul. 4, 2021. 2 pages. (Year: 2021).*
Saha et al. Evaluating the potential for undesired genomic effect of the piggyBack transposon system in human cells. Jan. 20, 2015. Nucleic Acids Research. Vol. 43, No. 3, p. 1770-1782. (Year: 2015).*

* cited by examiner

*Primary Examiner* — Channing S Mahatan

(57) ABSTRACT

A kit for constructing a transposon is provided. The kit comprises five plasmids, each of which consists essentially of a gene cassette linked or not linked to a terminal repeat. The kit is useful in selecting the type of piggyBac that exhibits the least enhancer activity in the host cells.

12 Claims, 3 Drawing Sheets

Specification includes a Sequence Listing.

SEQUENCE LISTING

<160> NUMBER OF SEQ ID NOS: 12

<210> SEQ ID NO 1
<211> LENGTH: 244
<212> TYPE: DNA
<213> ORGANISM: Artificial Sequence
<220> FEATURE:
<223> OTHER INFORMATION: miniL (the left terminal inverted repeat of
      mini-piggyBac)

<400> SEQUENCE: 1
ttaaccctag aaagataatc atattgtgac gtacgttaaa gataatcatg tgtaaaattg      60
acgcatgtgt tttatcggtc tgtatatcga ggtttattta ttaatttgaa tagatattaa     120
gttttattat atttacactt acatactaat aataaattca acaaacaatt tatttatgtt     180
tatttattta ttaaaaaaaa caaaaactca aaatttcttc tataaagtaa caaaacttt      240 atcg                                                                  244

<210> SEQ ID NO 2
<211> LENGTH: 313
<212> TYPE: DNA
<213> ORGANISM: Artificial Sequence
<220> FEATURE:
<223> OTHER INFORMATION: miniR (the right terminal inverted repeat of
      mini-piggyBac)

<400> SEQUENCE: 2
gctatctata acaagaaaat atatatataa taagttatca cgtaagtaga acatgaaata      60
acaatataat tatcgtatga gttaaatctt aaaagtcacg taaagataa tcatgcgtca     120 ttttgactca cgcggtcgtt atagttcaaa atcagtgaca cttaccgcat tgacaagcac     180
gcctcacggg agctccaagc ggcgactgag atgtcctaaa tgcacagcga cggattcgcg     240
ctatttagaa agagagagca atatttcaag aatgcatgcg tcaattttac gcagactatc     300
tttctagggt taa                                                        313

<210> SEQ ID NO 3
<211> LENGTH: 67
<212> TYPE: DNA
<213> ORGANISM: Artificial Sequence
<220> FEATURE:
<223> OTHER INFORMATION: microL (the left terminal inverted repeat of
      micro-piggyBac)

<400> SEQUENCE: 3
ttaaccctag aaagataatc atattgtgac gtacgttaaa gataatcatg cgtaaaattg      60
acgcatg                                                               67

<210> SEQ ID NO 4
<211> LENGTH: 40
<212> TYPE: DNA
<213> ORGANISM: Artificial Sequence
<220> FEATURE:
<223> OTHER INFORMATION: microR (the right terminal inverted repeat of
      micro-piggyBac)

<400> SEQUENCE: 4
gcatgcgtca attttacgca gactatcttt ctagggttaa                           40

<210> SEQ ID NO 5
<211> LENGTH: 35
<212> TYPE: DNA
<213> ORGANISM: Artificial Sequence
<220> FEATURE:
<223> OTHER INFORMATION: Minimal promoter

<400> SEQUENCE: 5
atctagaggg tatataatgg aagctcgact tccag       35

<210> SEQ ID NO 6
<211> LENGTH: 107
<212> TYPE: DNA
<213> ORGANISM: Artificial Sequence
<220> FEATURE:
<223> OTHER INFORMATION: microLR (a DNA sequence consist of both left
      and the right terminal inverted repeats of micro-piggyBac)

<400> SEQUENCE: 6
ttaaccctag aaagataatc atattgtgac gtacgttaaa gataatcatg cgtaaaattg       60
acgcatggca tgcgtcaatt ttacgcagac tatctttcta gggttaa       107

<210> SEQ ID NO 7
<211> LENGTH: 82
<212> TYPE: DNA
<213> ORGANISM: Artificial Sequence
<220> FEATURE:
<223> OTHER INFORMATION: DNA fragment miniP

<400> SEQUENCE: 7
ggtaccgagc tcttacgcgt gctagcccgg gctcgagatc tagagggtat ataatggaag       60
ctcgacttcc agaagcttgg ca       82

<210> SEQ ID NO 8
<211> LENGTH: 264
<212> TYPE: DNA
<213> ORGANISM: Artificial Sequence
<220> FEATURE:
<223> OTHER INFORMATION: DNA fragment miniL

<400> SEQUENCE: 8
atcgggtacc ttaaccctag aaagataatc atattgtgac gtacgttaaa gataatcatg       60
tgtaaaattg acgcatgtgt tttatcggtc tgtatatcga ggtttattta ttaatttgaa       120
tagatattaa gttttattat atttacactt acatactaat aataaattca acaaacaatt       180
tatttatgtt tatttattta ttaaaaaaaa caaaaactca aaatttcttc tataaagtaa       240
caaaactttt atcgctcgag atct       264

<210> SEQ ID NO 9
<211> LENGTH: 334
<212> TYPE: DNA
<213> ORGANISM: Artificial Sequence
<220> FEATURE:
<223> OTHER INFORMATION: DNA fragment miniR

<400> SEQUENCE: 9
atcgggtacc gctatctata acaagaaaat atatatataa taagttatca cgtaagtaga       60
acatgaaata acaatataat tatcgtatga gttaaatctt aaaagtcacg taaaagataa       120
tcatgcgtca ttttgactca cgcggtcgtt atagttcaaa atcagtgaca cttaccgcat       180
tgacaagcac gcctcacggg agctccaagc ggcgactgag atgtcctaaa tgcacagcga       240
cggattcgcg ctatttagaa agagagagca atatttcaag aatgcatgcg tcaatttttac       300 gcagactatc tttctagggt taagctcgag atct       334

```
<210> SEQ ID NO 10
<211> LENGTH: 152
<212> TYPE: DNA
<213> ORGANISM: Artificial Sequence
<220> FEATURE:
<223> OTHER INFORMATION: DNA fragment microLR

<400> SEQUENCE: 10
atcgggtacc ttaaccctag aaagataatc atattgtgac gtacgttaaa gataatcatg      60
cgtaaaattg acgcatgctc gagatttaaa tccaccgcgg tggcatgcgt caattttacg     120
cagactatct ttctagggtt aactcgagat ct                                    152

<210> SEQ ID NO 11
<211> LENGTH: 87
<212> TYPE: DNA
<213> ORGANISM: Artificial Sequence
<220> FEATURE:
<223> OTHER INFORMATION: DNA fragment microL

<400> SEQUENCE: 11
atcgggtacc ttaaccctag aaagataatc atattgtgac gtacgttaaa gataatcatg      60
cgtaaaattg acgcatgctc gagatct                                          87

<210> SEQ ID NO 12
<211> LENGTH: 71
<212> TYPE: DNA
<213> ORGANISM: Artificial Sequence
<220> FEATURE:
<223> OTHER INFORMATION: DNA fragment microR

<400> SEQUENCE: 12
atcgggtacc ccaccgcggt ggcatgcgtc aattttacgc agactatctt tctagggtta      60
actcgagatc t                                                           71
```

KIT FOR CONSTRUCTING TRANSPOSON AND USE THEREOF

CROSS REFERENCE TO RELATED APPLICATION

This application is a U.S. National Stage Filing under 35 U.S.C. 371 from International Patent Application Serial No. PCT/CN2016/077323, filed Mar. 25, 2016, and published on Sep. 28, 2017, the disclosure of which are incorporated by reference herein in their entireties.

BACKGROUND OF THE INVENTION

1. Field of the Invention

The present disclosure in general relates to the field of transposon. More particularly, the present disclosure relates to kits and methods for selecting the most suitable type of terminal repeats to construct a piggyBac-based gene transfer vector.

2. Description of Related Art

DNA transposons that translocate by excision from a donor site and insertion into a target site are often used for genome engineering by insertional mutagenesis and transgenesis. PiggyBac (PB) is a class II transposon that precisely and efficiently transposes between vectors and chromosomes via a "cut and paste" mechanism. PB transposon exists in nature as a gene that encodes a transposase and is flanked by inverted terminal repeat (ITR) sequences. During the transposition, the transposase recognizes the ITR sequences and catalyzes the excision of the transposon from the original locus followed by efficiently integrating it into TTAA target sites.

Based on the "cut and paste" mechanism, the PB transposon provides a powerful means to efficiently integrate the exogenous gene into the host chromosome; accordingly, resulting in a long-term and stable expression of the exogenous gene in the host cell. Structurally, the exogenous gene is inserted between the ITR sequences. The transposition activity is enabled by providing the transposase from a separate vector. This arrangement permits the exogenous gene between the two ITRs to be easily mobilized into target genomes.

However, it has been reported that in addition to the transposition activity, the ITR may function as an enhancer to stimulate the expression of endogenous genes near the insertion site. The cis-acting enhancement likely disturbs the global gene expression pattern, and thus, leading to an undesired result.

There are two type of piggyBac terminal inverted repeats, mini-piggyBac (a longer version) and micro-piggyBac (a shortened version). Accordingly, there exists in the related art a need for a selection system to select the most appropriate type of piggyBac that efficiently introduce an exogenous gene into a cell enabling stable without affecting the global gene expression; the introduced cell constantly expressing the exogenous gene in a desired manner may be used in a cell therapy so as to prevent or treat different diseases.

SUMMARY

The following presents a simplified summary of the disclosure in order to provide a basic understanding to the reader. This summary is not an extensive overview of the disclosure and it does not identify key/critical elements of the present invention or delineate the scope of the present invention. Its sole purpose is to present some concepts disclosed herein in a simplified form as a prelude to the more detailed description that is presented later.

As embodied and broadly described herein, one aspect of the disclosure is directed to a kit, which is useful in selecting a terminal repeat for constructing a transposon that introduces an exogenous gene into the host cells without affecting the global gene expression therein. According to the embodiments of the present disclosure, the kit comprises five plasmids, in which the control plasmid consists essentially of, a gene cassette, which comprises a promoter of SEQ ID NO: 5 and a reporter gene operably linked to the promoter;

the first plasmid consists essentially of, the gene cassette and a first terminal repeat of SEQ ID NO: 1, which is disposed upstream of the gene cassette;

the second plasmid consists essentially of, the gene cassette and a second terminal repeat of SEQ ID NO: 2, which is disposed upstream of the gene cassette;

the third plasmid consists essentially of, the gene cassette and a third terminal repeat of SEQ ID NO: 3, which is disposed upstream of the gene cassette; and the fourth plasmid consists essentially of, the gene cassette and a fourth terminal repeat of SEQ ID NO: 4, which is disposed upstream of the gene cassette.

According to some embodiments of the present disclosure, the reporter gene comprised in the present gene cassette encodes a fluorescent protein. According to other embodiments of the present disclosure, the reporter gene comprised in the present gene cassette encodes a luminescent protein.

According to certain embodiments, the host cells are mammalian origin or insect origin. In one embodiment, the host cells are immune cells selected from the group consisting of, T cells, B cells, natural killer cells, dendritic cells, macrophages, and mast cells. In another embodiment, the host cells are stem cells derived from bone marrow, adipose tissue, peripheral blood, umbilical cord blood, or dental pulp. In still another embodiment, the host cells are epithelial cells.

The second aspect of the present disclosure pertains to a method of constructing a transposon by selecting a preferable pair of terminal repeats for construction using the kit of the present disclosure. When the transposon constructed in accordance with the present method is co-expressed with a transposase that recognizes the ITR sequences of the transposon in the host cells, the transposon is capable of introducing the exogenous gene into the host cells without affecting the expression level of the genes close to the integration site. The method comprises the steps of, (1) respectively transfecting the host cells with the five plasmids (i.e., the control plasmid, and the first to the fourth plasmids) of the present kit;

(2) determining a control expression level of the reporter gene of the control plasmid in the host cells and respective expression levels of the respective reporter genes of the first to the fourth plasmids in the host cells; and (3) constructing the transposon based on the expression levels determined in the step (2).

According to the embodiments of the present disclosure, the transposon constructed by the present method consists essentially of, an expression cassette comprising a non-prokaryotic promoter and the exogenous gene operably linked to the non-prokaryotic promoter;

a first selected terminal repeat; and a second selected terminal repeat.

According to the embodiments of the present disclosure, the first selected terminal repeat is one of the first to the fourth terminal repeats that elicits an expression level closest to the control expression level. According to some embodiments of the present disclosure, the first selected terminal repeat is the first or the third terminal repeat; in these embodiments, the first selected terminal repeat is disposed upstream of the expression cassette, and the second selected terminal repeat is the second or the fourth terminal repeat that is disposed downstream of the gene cassette. According to other embodiments of the present disclosure, the first selected terminal repeat is the second or the fourth terminal repeat; in these embodiments, the first selected terminal repeat is disposed downstream of the expression cassette, and the second selected terminal repeat is the first or the third terminal repeat that is disposed upstream of the gene cassette.

In certain embodiments of the present disclosure, once the first selected terminal repeat is determined, the second selected terminal repeat is selected based on the expression levels in the host cells. More specifically, when the first selected terminal repeat is the first or the third terminal repeat, the second selected terminal repeat is the second or the fourth terminal repeat that elicits an expression level closer to the control expression level. Alternatively, when first selected terminal repeat is the second or the fourth terminal repeat, the second selected terminal repeat is the first or the third terminal repeat that elicits an expression level closer to the control expression level.

In other embodiments of the present disclosure, the second selected terminal repeat is determined in accordance with the first selected terminal repeat. According to one embodiment, the first selected terminal repeat is the first terminal repeat, and the second selected terminal repeat is the second terminal repeat. According to another embodiment, the first selected terminal repeat is the second terminal repeat, and the second selected terminal repeat is the first terminal repeat. According to still another embodiment, the first selected terminal repeat is the third terminal repeat, and the second selected terminal repeat is the fourth terminal repeat. According to further another embodiment, the first selected terminal repeat is the fourth terminal repeat, and the second selected terminal repeat is the third terminal repeat.

The non-prokaryotic promoter of the expression cassette can be an inducible promoter or a constitutive promoter. Non-limiting constitutive promoter includes, cytomegalovirus (CMV) promoter, rous sarcoma virus (RSV) promoter, simian virus (SV40) promoter, mouse mammary tumor virus (MMTV) promoter, phosphoglycerate kinase (PGK) promoter, chicken beta-active promoter, elongation factor 1-alpha (EF1-α) promoter, human H1 promoter, and U6 promoter.

Many of the attendant features and advantages of the present disclosure will becomes better understood with reference to the following detailed description considered in connection with the accompanying drawings.

BRIEF DESCRIPTION OF THE DRAWINGS

The present description will be better understood from the following detailed description read in light of the accompanying drawings, where.

Figure 1A:
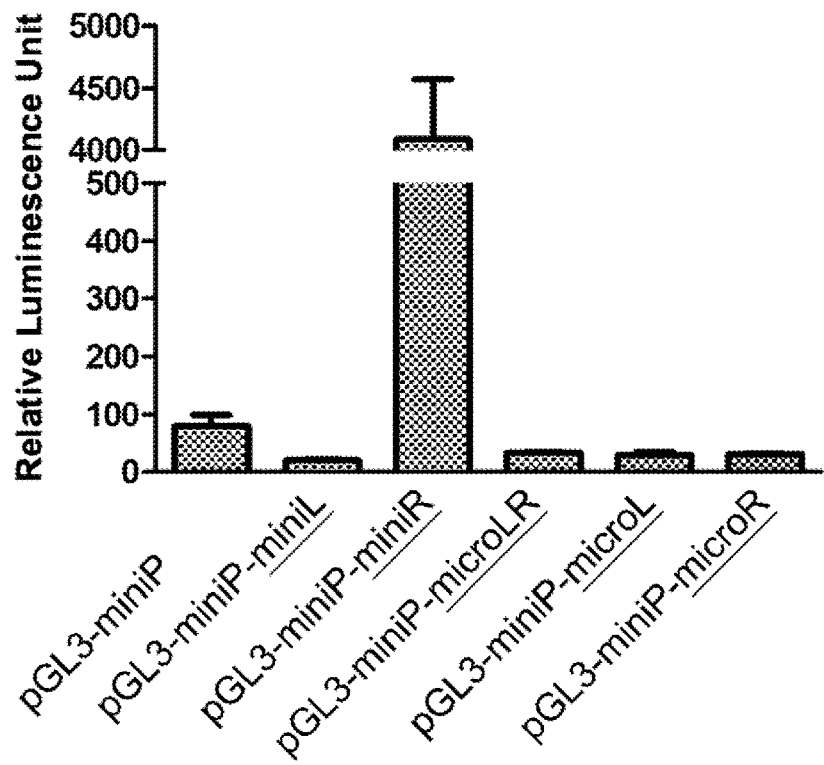
FIGS. 1A-1C are histograms depicting the enhancer activities of specified plasmids in SF9 cell (FIG. 1A), embryonic stem cell (ESC, FIG. 1B), or HEK293 cell (FIG. 1C) according to Example 1 of the present disclosure.

In accordance with common practice, the various described features/elements are not drawn to scale but instead are drawn to best illustrate specific features/elements relevant to the present invention.

DETAILED DESCRIPTION OF THE INVENTION

The detailed description provided below in connection with the appended drawings is intended as a description of the present examples and is not intended to represent the only forms in which the present example may be constructed or utilized. The description sets forth the functions of the example and the sequence of steps for constructing and operating the example. However, the same or equivalent functions and sequences may be accomplished by different examples.

For convenience, certain terms employed in the specification, examples and appended claims are collected here. Unless otherwise defined herein, scientific and technical terminologies employed in the present disclosure shall have the meanings that are commonly understood and used by one of ordinary skills in the art. Also, unless otherwise required by context, it will be understood that singular terms shall include plural forms of the same and plural terms shall include the singular. Specifically, as used herein and in the claims, the singular forms "a" and "an" include the plural reference unless the context clearly indicates otherwise. Also, as used herein and in the claims, the terms "at least one" and "one or more" have the same meaning and include one, two, three, or more.

Notwithstanding that the numerical ranges and parameters setting forth the broad scope of the invention are approximations, the numerical values set forth in the specific examples are reported as precisely as possible. Any numerical value, however, inherently contains certain errors necessarily resulting from the standard deviation found in the respective testing measurements. Also, as used herein, the term "about" generally means within 10%, 5%, 1%, or 0.5% of a given value or range. Alternatively, the term "about" means within an acceptable standard error of the mean when considered by one of ordinary skills in the art. Other than in the operating/working examples, or unless otherwise expressly specified, all of the numerical ranges, amounts, values and percentages such as those for quantities of materials, durations of times, temperatures, operating conditions, ratios of amounts, and the likes thereof disclosed herein should be understood as modified in all instances by the term "about". Accordingly, unless indicated to the contrary, the numerical parameters set forth in the present disclosure and attached claims are approximations that can vary as desired. At the very least, each numerical parameter should at least be construed in light of the number of reported significant digits and by applying ordinary rounding techniques.

As used herein, the term "transposon" refers to a polynucleotide that is able to excise from a donor polynucleotide, for instance, a vector, and integrate itself into a target site, for instance, a cell's genomic or extrachromosomal DNA. A transposon includes a polynucleotide that includes a nucleic acid sequence flanked by cis-acting nucleotide sequences; if at least one cis-acting nucleotide sequence is positioned 5' to the nucleic acid sequence, and at least one cis-acting nucleotide sequence is positioned 3' to the nucleic acid sequence. Cis-acting nucleotide sequences include at least one ITR at each end of the transposon, to which a transposase, preferably a member of the mammalian piggyBac family of transposases, binds. In certain preferred embodiments, the transposon is a mammalian piggyBac transposon.

As used herein, the term "transposase" refers to a polypeptide that catalyzes the excision of a transposon from a polynucleotide and the subsequent integration of the transposon into the genomic or extrachromosomal DNA of a target cell. Preferably, the transposase binds an inverted sequence or a direct repeat. The transposase may be present as a polypeptide. Alternatively, the transposase is present as a polynucleotide that includes a coding sequence encoding a transposase.

As used herein, the term "plasmid" refers to circular, double-stranded DNA capable of inserting a foreign DNA fragment.

As used herein, the term "immune cell" refers to cells that play a role in the immune response. Immune cells are of hematopoietic origin, and include lymphocytes, such as B cells and T cells; natural killer cells; myeloid cells, such as monocytes, macrophages, eosinophils, mast cells, basophils, and granulocytes.

The term "stem cell" as used herein refers to an undifferentiated cell that can differentiate without limitation into various cell types constituting the tissues of an organism so as to produce specialized cells of tissues and organs. The stem cells are totipotent or multipotent cells. The stem cell can divides either into two daughter stem cells, or into one daughter stem cell and one original stem cell. Later, the cells proliferate into mature and complete cells of tissues.

As used herein, the term "mesenchymal stem cell" refers to a multipotent stem cell that can differentiate into adipocytes, osteocytes, chondrocytes, myocytes, neurons and cardiomyocytes. The mesenchymal stem cells are identified by the spiral shape and the expression of the surface markers CD73(+), CD105(+), CD34(−) and CD45(−).

The term "epithelial cell" as used herein refers to a cuboidal-shaped, nucleated cell covering the free surface (cutaneous, mucous or serous) of an organ or lining a tube or cavity in an animal body, and is consistent with the art-recognized definition of epithelial cells in epithelium. A layer of epithelial cells generally functions to provide a protective lining and/or surface that may also be involved in transport processes.

The term "inducible promoter" as used herein refers to promoters that selectively express a coding sequence or functional RNA in response to the presence of an endogenous or exogenous stimulus. More specifically, the term "inducible promoter" as used herein denotes a promoter whose activity can be increased upon a physical or chemical stimulus; for example, a chemical compound (e.g., chemical inducer), an environmental stimulus (e.g., temperature and light), a hormonal stimulus, and/or a developmental signaling.

As used herein, the term "constitutive promoter" refers to a promoter whose activity is maintained at a relatively constant level in all cells of an organism with little or no regard to cell environmental conditions (as the concentration of a substrate).

The term "construct" is used herein in its broad sense, referring to a linear or circular nucleotide sequence such as DNA that has been assembled from more than one segments of nucleotide sequence which have been isolated from a natural source or have been chemically synthesized, or combinations thereof.

As used herein, the term "minimal promoter" refers to the smallest piece of a promoter, such as a TATA element, that can support any transcription. A minimal promoter typically has greatly reduced promoter activity in the absence of upstream or downstream activator (e.g., an enhancer). In the presence of a suitable transcription factor, a minimal promoter can function to permit transcription.

The objective of the present disclosure aims at providing a means to construct a transposon that introduces an exogenous gene into the host cells without affecting the global gene expression therein. Accordingly, the first aspect of the present disclosure is directed to a kit comprising five plasmids, in which the control plasmid (hereinafter referred to as "pGL3-miniP") consists essentially of, a gene cassette, which comprises a promoter of SEQ ID NO: 5 and a reporter gene operably linked to the promoter;

the first plasmid (hereinafter referred to as "pGL3-miniP-miniL") consists essentially of, the gene cassette and a first terminal repeat of SEQ ID NO: 1, which is disposed upstream of the gene cassette;

the second plasmid (hereinafter referred to as "pGL3-miniP-miniR") consists essentially of, the gene cassette and a second terminal repeat of SEQ ID NO: 2, which is disposed upstream of the gene cassette;

the third plasmid (hereinafter referred to as "pGL3-miniP-microL") consists essentially of, the gene cassette and a third terminal repeat of SEQ ID NO: 3, which is disposed upstream of the gene cassette; and the fourth plasmid (hereinafter referred to as "pGL3-miniP-microR") consists essentially of, the gene cassette and a fourth terminal repeat of SEQ ID NO: 4, which is disposed upstream of the gene cassette.

Structurally, each of the five plasmids consists essentially of a gene cassette, which comprises a minimal promoter and a reporter gene operably linked to the minimal promoter. According to the embodiments of the present disclosure, the minimal promoter comprised in the present gene cassette has a nucleotide sequence of SEQ ID NO: 5. In some embodiments, the reporter gene encodes a fluorescent protein; for example, green fluorescence protein (GFPs), enhanced green fluorescence protein (EGFP), *Discosoma* sp. red fluorescent protein (DsRed), blue fluorescence protein (BFP), enhanced yellow fluorescent proteins (EYFP), *Anemonia majano* fluorescent protein (amFP), *Zoanthus* fluorescent protein (zFP), *Discosoma* fluorescent protein (dsFP), and *Clavularia* fluorescent protein (cFP). In other embodiments, the reporter gene encodes a luminescent protein, such as luciferase, horseradish peroxidase, quantum dots, or a combination thereof. According to one working example, the reporter gene of the present gene cassette encodes luciferase.

In addition to the gene cassette, each of the first to fourth plasmids (i.e., pGL3-miniP-miniL, pGL3-miniP-miniR, pGL3-miniP-microL, and pGL3-miniP-microR) further includes, a terminal repeat, which is disposed upstream of the gene cassette. Specifically, the plasmid pGL3-miniP-miniL consists essentially of, the gene cassette and the first terminal repeat, which is derived from the 5'-terminal repeat region of mini-piggyBac and has the nucleotide sequence of SEQ ID NO: 1 (hereinafter referred to as "miniL"). The plasmid pGL3-miniP-miniR consists essentially of, the gene cassette and the second terminal repeat, which is derived from the 3'-terminal repeat region of mini-piggyBac and has the nucleotide sequence of SEQ ID NO: 2 (hereinafter referred to as "miniR"). The plasmid pGL3-miniP-microL consists essentially of, the gene cassette and the third terminal repeat, which is derived from the 5'-terminal repeat region of micro-piggyBac and has the nucleotide sequence of SEQ ID NO: 3 (hereinafter referred to as "microL"). The plasmid pGL3-miniP-microR consists essentially of, the gene cassette and the fourth terminal repeat, which is derived from the 3'-terminal repeat region of micro-piggy-Bac and has the nucleotide sequence of SEQ ID NO: 4 (hereinafter referred to as "microR").

As described above, the present kit is useful for selecting a preferable pair of terminal repeats for constructing a transposon. Accordingly, the second aspect of the present disclosure pertains to a method of constructing a transposon by use of the present kit. The constructed transposon is characterized in that when being co-expressed with a transposase in the host cells, it is capable of introducing an exogenous gene into the host cells without affecting the expressions of the host gene and the exogenous gene. According to the embodiments of the present disclosure, the method comprises the steps of, (1) respectively transfecting the host cells with the five plasmids of the present kit (i.e., pGL3-miniP, pGL3-miniP-miniL, pGL3-miniP-miniR, pGL3-miniP-microL, and pGL3-miniP-microR);

(2) determining a control expression level of the reporter gene of the control plasmid (i.e., pGL3-miniP) in the host cells and respective expression levels of the respective reporter genes of the first to the fourth plasmids (i.e., pGL3-miniP-miniL, pGL3-miniP-miniR, pGL3-miniP-microL, and pGL3-miniP-microR) in the host cells; and (3) constructing the transposon based on the expression levels determined in the step (2).

Before practicing the present method, the host cells are grown to confluence followed by being suspended and seeded into five wells (i.e., the first, second, third, fourth, and fifth wells) of a microplate, in which each well has substantially equal numbers of cells for use in the present method. Host cells are chosen in accordance with the intended purpose, and they can be either mammalian origin or insect origin. According to one embodiment of the present disclosure, the host cells are human immune cells selected from the group consisting of, T cells, B cells, natural killer cells, dendritic cells, macrophages, and mast cells. According to another embodiment of the present disclosure, the host cells are human stem cells derived from bone marrow, adipose tissue, peripheral blood, umbilical cord blood, or dental pulp. According to still another embodiment of the present disclosure, the host cells are human epithelial cells. According to still further embodiment of the present disclosure, the host cells are insect cells derived from *Spodoptera frugiperda*.

In step (1), the five plasmids are respectively introduced into the host cells seeded in the first to fifth wells of a culture plate. The plasmids are introduced into the host cells by a means that includes, but is not limited to, chemical method (such as, calcium phosphate, highly branched organic compound/dendrimer, liposome, and cationic polymer treatments), electroporation, cell squeezing (gently squeezing cell membrane), sonoporation (inducing pore formation in cell membrane by high-intensity ultrasound), optical transfection (generating a tiny hole in cell membrane by highly focused laser), impalefection (DNA bound to a surface of a nanofiber that is inserted into a cell), gene gun (DNA coupled to a nanoparticle of an inert solid that is then "shot" directly into the target cell's nucleus), magnetofection/magnet assisted transfection (using magnetic force to deliver DNA into target cells), and/or viral method/viral transduction (using viruses as a carrier to deliver DNA into target cells). According to one working example of the present disclosure, the five plasmids are respectively introduced into the host cells via chemical method (FuGENE® HD transfection). According to another working example of the present disclosure, the five plasmids are respectively introduced into the host cells via electroporation (Nucleofection).

In the step (2), the expression levels of reporter genes in the host cells respectively transfected with the five plasmids are measured. Various assays may be used to determine the expressed level of the reporter genes. According to some embodiments of the present disclosure, the reporter gene encodes a fluorescent protein, thus the expression can be determined by use of the flow cytometry technique and/or by measuring the fluorescence intensity emitted therefrom. According to other embodiments of the present disclosure, the reporter gene encodes a luminescent protein, which can be detected by measuring the luminescence intensity. In one specific example, the reporter gene is the fire fly luciferase gene. As familiar by any skilled artisans, luciferase catalyzes the oxidation of luciferin, and the emission intensity can be detected by the spectrometer.

In step (3), the transposon is constructed based on the expression levels of the reporter genes in host cells determined in the step (2). Specifically, one plasmid is selected from the plasmids pGL3-miniP-miniL, pGL3-miniP-miniR, pGL3-miniP-microL, and pGL3-miniP-microR for subsequent construction of the transposon, in which the expression level of the reporter gene in the host cells transfected with the selected plasmid is comparable to that of the host cells transfected with the plasmid pGL3-miniP. The expression level of the plasmid pGL3-miniP of the present kit is set as the expression background. Then, the expression levels of the plasmids pGL3-miniP-miniL, pGL3-miniP-miniR, pGL3-miniP-microL, and pGL3-miniP-microR are compared to the expression background. The higher expression level of the reporter gene indicates the terminal repeat carried by that plasmid is more effective in enhancing the expression of the genes. In general, the enhancer activity of the terminal repeat varies with the choice of the host cells. According to one embodiment of the present disclosure, except the terminal repeat miniR, all the terminal repeats including miniL, microL and microR exhibit low enhancer activities in the insect cells. According to another embodiment of the present disclosure, among the terminal repeats tested, the terminal repeat microR exhibits the lowest enhancer activity in human ESCs and epithelial cells, and T cells. According to still another embodiment of the present disclosure, the terminal repeat miniL is least effective in enhancing the reporter gene expression, among the terminal repeats tested in the human mesenchymal stem cells (MSCs).

Then, the terminal repeat of the selected plasmid is used to construct the present transposon. Structurally, the constructed transposon consists essentially of, a 5'-terminal repeat, an expression cassette, and a 3'-terminal repeat, in sequence, from 5'-end to 3'-end. The expression cassette comprises an exogenous gene, which is intended to be introduced into the host cells and expressed therein, and a non-prokaryotic promoter used to drive the expression of the target gene. Depending on the intended applications, the exogenous gene can be a reporter gene or a therapeutic gene; non-limiting examples of therapeutic gene include cytotoxic gene, immunomodulatory gene, anti-angiogenic gene, anti-inflammatory gene, anti-proliferation gene, tumor suppressor gene, pro-differentiation gene, and hormone gene. As to the non-prokaryotic promoter, it can be an inducible promoter, whose performance is not conditioned to endogenous factors but to environmental conditions and external stimuli that can be artificially controlled. The example of the inducible promoter includes, but is not limited to, heat shock inducible promoter, metallothionin promoter, ecdysone-inducible promoter, FKBP dimerization inducible promoter, Gal4-estrogen receptor fusion protein regulated promoter, steroid inducible promoter, streptogram in responsive promoter, and tetracycline regulated promoter. Alternatively, the non-prokaryotic promoter can be a constitutive promoter selected from the group consisting of, cytomegalovirus (CMV) promoter, rous sarcoma virus (RSV) promoter, simian virus (SV40) promoter, mouse mammary tumor virus (MMTV) promoter, phosphoglycerate kinase (PGK) promoter, chicken beta-active promoter, elongation factor 1-alpha (EF1-α) promoter, human H1 promoter, and U6 promoter.

In terms of the 5'-terminal repeat and the 3'-terminal repeat, one of them is the terminal repeat of the selected plasmid. More specifically, when the terminal repeat miniL or microL elicits an expression level closest to the control expression level, it is employed as the 5'-terminal repeat, which is disposed upstream of the expression cassette; in this case, one of the terminal repeats miniR and microR is chosen as the 3'-terminal repeat, which is disposed downstream of the expression cassette. According to some embodiments of the present disclosure, the choice of the terminal repeats miniR and microR depends on their expression levels in the host cells, in which the one that elicits an expression level closer to the control expression level is chosen as the 3'-terminal repeat. According to other embodiments of the present disclosure, the choice of the terminal repeats miniR and microR depends on the 5'-terminal repeat; that is, when the terminal repeat miniL is employed as the 5'-terminal repeat, then the miniR is chosen as the 3'-terminal repeat; or when the terminal repeat microL serves as the 5'-terminal repeat, then the microR is chosen as the 3'-terminal repeat.

Alternatively, when the terminal repeat miniR or microR elicits an expression level closest to the control expression level, it is selected as the 3'-terminal repeat, which is disposed downstream of the expression cassette; in this case, one of the terminal repeats miniL and microL is chosen as the 5'-terminal repeat, which is disposed upstream of the expression cassette. According to certain embodiments of the present disclosure, the choice of the terminal repeats miniL and microL depends on their expression levels in the host cells, in which the one that elicits an expression level closer to the control expression level is chosen as the 5'-terminal repeat. According to other embodiments of the present disclosure, the choice of the terminal repeats miniL and microL depends on the 3'-terminal repeat; that is, when the terminal repeat miniR is employed as the 3'-terminal repeat, then the miniL is chosen as the 5'-terminal repeat; or, when the terminal repeat microR is selected as the 3'-terminal repeat, then the microL is chosen as the 5'-terminal repeat.

Accordingly, the present transposon may be constructed in the form of (i) miniL-expression cassette-miniR (as the form of the transposon mini-piggyBac), (ii) miniL-expression cassette-microR, (iii) microL-expression cassette-microR (as the form of the transposon micro-piggyBac), or (iv) microR-expression cassette-miniL, depending on the host cell intended to be used.

The present transposon is advantageous in that when co-expressed with a transposase recognizing the 5'-terminal repeat and the 3'-terminal repeat of the present transposon, it may efficiently introduce a gene of interest (e.g., the therapeutic gene) into the host cells, without affecting the gene expression therein. Accordingly, the present transposon provides a potential means to treat various diseases, including the caner, the inflammatory disease, the immunodeficiency disease, the angiogenesis-associated disease, and the hormone-associated disease.

In general, a plasmid comprising the transposase is introduced simultaneously with the present transposon into the host cells so that the transposase and the present transposon are co-expressed therein. Alternatively, the transposase and the present transposon are comprised in the same polynucleotide, so that when the polynucleotide is introduced into the host cells, the transposon and the transposase are simultaneously expressed therein. Preferably, the transposon is a PB transposase.

The following Examples are provided to elucidate certain aspects of the present invention and to aid those of skilled in the art in practicing this invention. These Examples are in no way to be considered to limit the scope of the invention in any manner. Without further elaboration, it is believed that one skilled in the art can, based on the description herein, utilize the present invention to its fullest extent. All publications cited herein are hereby incorporated by reference in their entirety.

EXAMPLE

Materials and Methods
Cell Culture

The HEK293 cells were cultured in MEM medium containing 10% fetal bovine serum (FBS; Hyclone, South Logan, Utah, USA), 2 mM L-glutamine, 1× nonessential amino acids, 1× penicillin/streptomycin, and 1 mM sodium pyruvate. The ESCs were cultured in high-glucose DMEM medium containing 15% FBS, 2 mM GlutaMAX, 0.1 mM nonessential amino acids, 1× penicillin/streptomycin, 1 mM sodium pyruvate, 0.1 mM 2-mercaptoethanol, 10 mM HEPES, and $10^3$ U leukaemia inhibitory factor (LIF) on γ-irradiated mouse embryonic fibroblast (MEF) feeder cells. The Jurkat T cells were cultured in RPMI1640 medium containing 2 mM L-glutamine, 10% FBS, 1 mM sodium pyruvate, and 0.1 mM nonessential amino acids. The SF9 cells were cultured in EX-CELL® 420 serum medium. The MSCs WJMSC960531 obtained from human Wharton's jelly, were culture in MEM medium containing 20% FBS, 1× penicillin/streptomycin, 2 mM L-glutamine, and 4 ng/ml basic fibroblast growth factor (b-FGF). Except Sf9 cells that were cultured at 25° C. in an open air chamber, all cells were maintained at 37° C. with 5% $CO_2$.

Construction
pGL3-miniP

The pGL3-basic vector was digested with the restriction enzymes KpnI and XhoI. A DNA fragment miniP of SEQ ID NO: 7 was synthesized, double digested with the restriction enzymes KpnI and XhoI, and then ligated to the KpnI-XhoI-digested pGL3-basic vector. The produced plasmid was designated as pGL3-miniP, which comprised the minimal promoter of SEQ ID NO: 5.

pGL3-miniP-miniL

The plasmid pGL3-miniP was digested with the restriction enzymes KpnI and XhoI. A DNA fragment miniL of SEQ ID NO: 8 was synthesized, digested with the restriction enzymes KpnI and XhoI, and then ligated to the KpnI-XhoI-digested pGL-miniP. The produced plasmid was designated as pGL3-miniP-miniL, which comprised the terminal repeat of SEQ ID NO: 1.

pGL-miniP-miniR

The plasmid pGL3-miniP was digested with the restriction enzymes KpnI and XhoI. A DNA fragment miniR of SEQ ID NO: 9 was synthesized, double digested with the restriction enzymes KpnI and XhoI, and then ligated to the KpnI-XhoI-digested pGL-miniP. The produced plasmid was designated as pGL-miniP-miniR, which comprised the terminal repeat of SEQ ID NO: 2.

pGL3-miniP-microLR

The plasmid pGL3-miniP was digested with the restriction enzymes KpnI and XhoI. A DNA fragment microLR of SEQ ID NO: 10 was synthesized, double digested with the restriction enzymes KpnI and XhoI and then ligated to the KpnI-XhoI-digested pGL-miniP. The produced plasmid was designated as pGL3-miniP-microLR, which comprised the terminal repeat of SEQ ID NO: 6.

pGL3-miniP-microL

The plasmid pGL3-miniP was digested with the restriction enzymes KpnI and XhoI. A 96 bp DNA fragment containing microL of SEQ ID NO: 11 (the left TIR of micro piggyBac) was synthesized, double digested with the restriction enzymes KpnI and XhoI, and then ligated to the KpnI-XhoI-digested pGL-miniP. The produced plasmid was designated as pGL3-miniP-microL, which comprised the terminal repeat of SEQ ID NO: 3.

pGL3-miniP-microR

The plasmid pGL3-miniP was digested with the restriction enzymes KpnI and XhoI. A DNA fragment microR of SEQ ID NO: 12 was synthesized, digested with the restriction enzymes KpnI and XhoI, and then ligated to the KpnI-XhoI-digested pGL-miniP. The produced plasmid was designated as pGL3-mini-microR, which comprised the terminal repeat of SEQ ID NO: 4.

Enhancer Assay

The control, pPL-TK (Renilla Luciferase), was co-transfected with specified firefly luciferase constructs (i.e., pGL3-miniP, pGL3-miniP-microL, pGL3-miniP-microR, pGL3-miniP-microLR, pGL-miniP-miniR, and pGL3-miniP-miniL) by either Fugene (HEK293) or Nuclefection (Sf9, R1 ES cells, and Jurkat T cells). Forty-eight hours after transfection, cells were harvested and subjected to Dual-Luciferase assay (Promega) by following the manufacturing instruction.

Example 1

Enhancer Activity in Various Host Cells

Figure 1B:
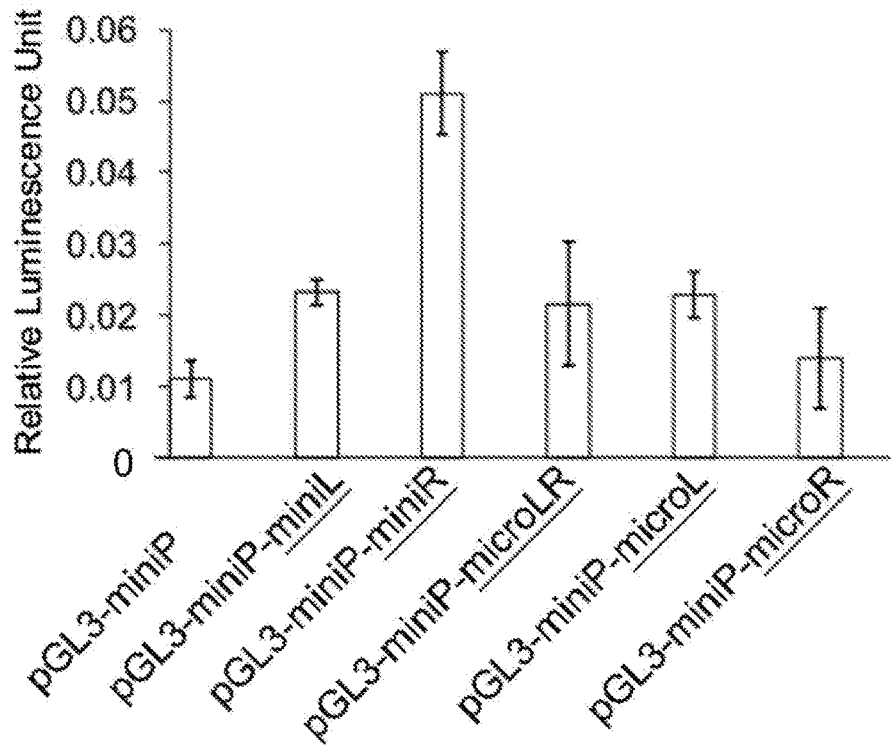
Figure 1C:
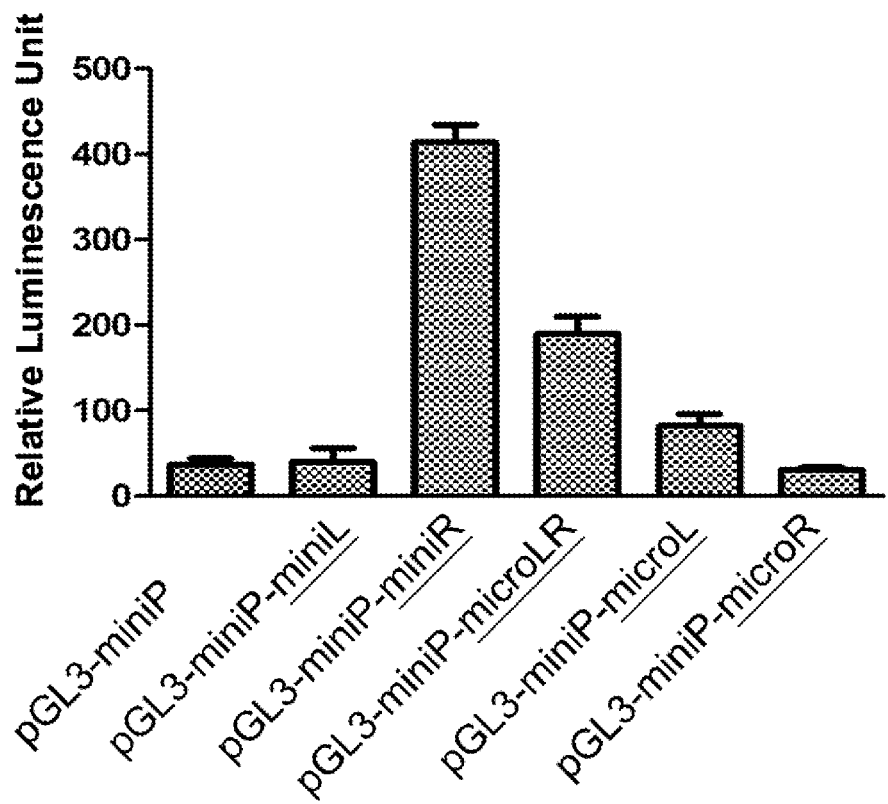
Figure 2:
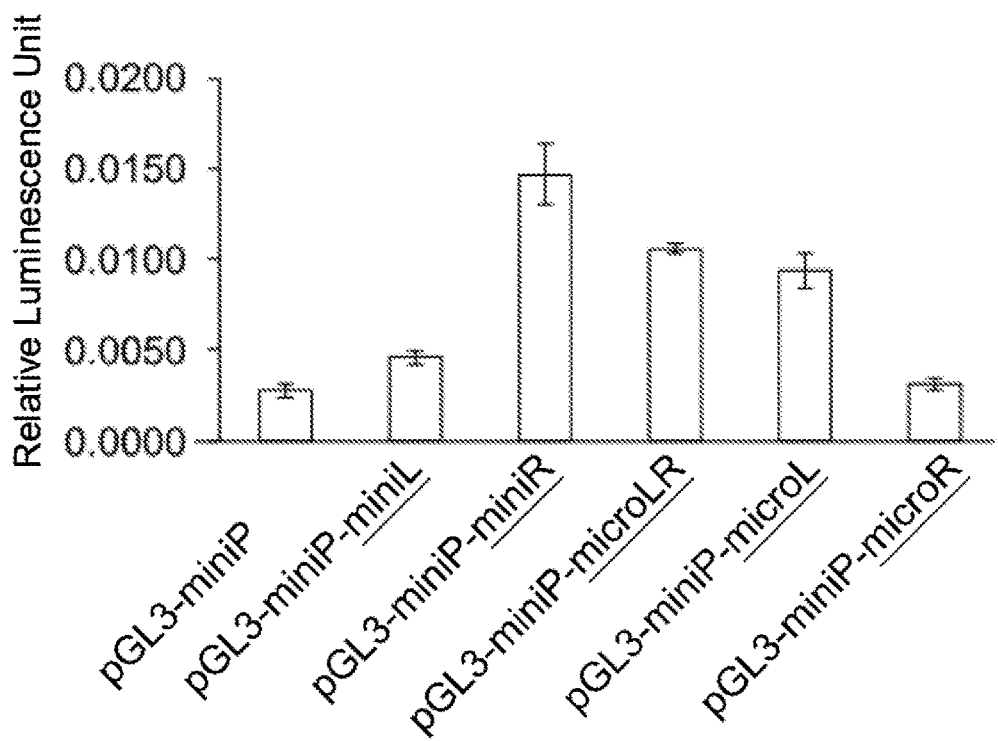
FIG. 2 is a histogram depicting the enhancer activities of specified plasmids in a therapeutic relevant cell, Jurkat T cell, according to Example 1 of the present disclosure.

In this example, one control plasmid (i.e., pGL3-miniP) and five tested plasmids (i.e., pGL3-miniP-miniL, pGL3-miniP-miniR, pGL3-miniP-microLR, pGL3-miniP-microL, and pGL3-miniP-microR) were respectively transfected into host cells, including Sf9 cell (FIG. 1A), ESC (FIG. 1B), HEK293 cell (FIG. 1C) and Jurkat T cell (FIG. 2). The enhancer activities of those plasmids were analyzed by the enhancer assay as described in "Materials and Methods".

As the data of FIG. 1A indicated, the Sf9 cells transfected with pGL3-miniP-miniR exhibited highest luciferase activity over that transfected with any of other plasmids (i.e., pGL3-miniP, pGL3-miniP-miniL, pGL3-miniP-microLR, pGL3-miniP-microL, and pGL3-miniP-microR). As to mammalian cells, among the plasmids that were tested, the expression level of luciferase conferred by the plasmid comprising pGL3-miniP-microR was closest to that comprising pGL3-miniP (ESC, FIG. 1B; HEK293 cell, FIG. 1C; Jurkat T cell, FIG. 2).

These data indicated that the enhancer activities of each terminal repeats differ in different host cells; according to the results, except the terminal repeat of SEQ ID NO: 2, all the terminal repeats tested (i.e., SEQ ID NOs: 1, 3, 4 and 6) did not possess enhancer activity in Sf9 cells. By contrast, among cells that are mammalian origin, including ESCs, HEK293 cells and Jurkat T cells, the terminal repeat of SEQ ID NO: 4 exhibited the least effect on enhancing the expression of reporter gene among the terminal repeats tested.

Example 2

Enhancer Activity in Human MSCs

Figure 3:
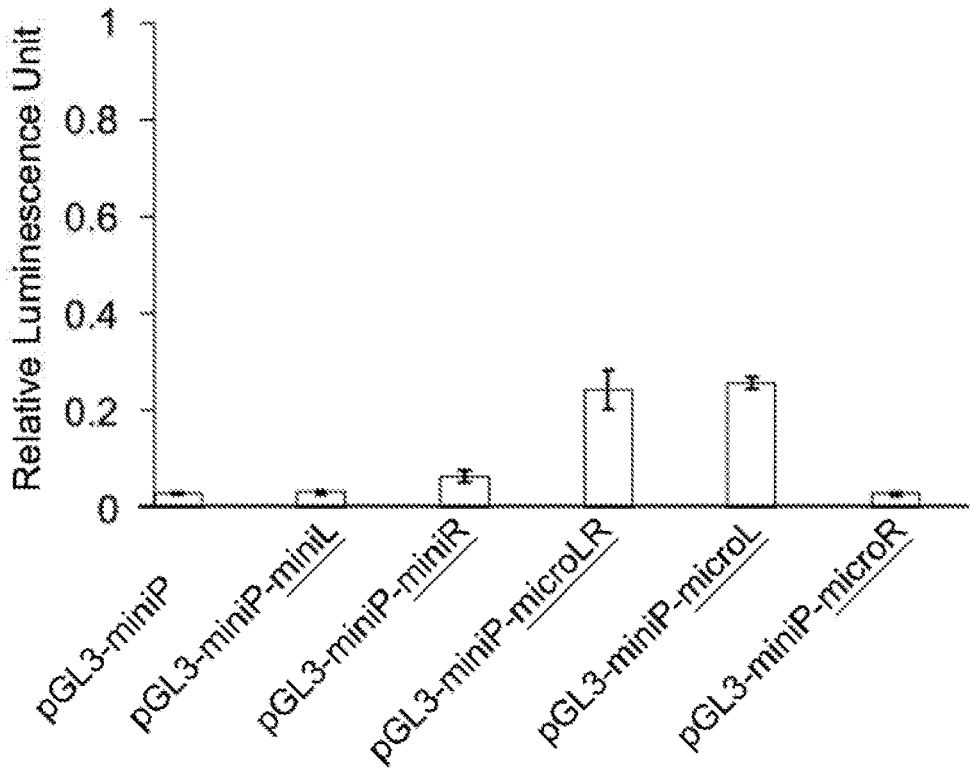
FIG. 3 is a histogram depicting the enhancer activities of specified plasmids in a therapeutic relevant cell, WJMSC960531 cell, according to Example 2 of the present disclosure.

The enhancer activities of the terminal repeats were also evaluated in human MSCs derived from Wharton's jelly. Results are depicted in FIG. 3.

Compared with the control group, the terminal repeats of SEQ ID NOs: 3 and 6 may respectively enhance the expression of the reporter genes, whereas neither the terminal repeats of SEQ ID NOs: 1 nor 4 (especially SEQ ID NO: 1) possessed significant enhancer activity in the MSCs tested.

Taken together, the data suggested that the terminal inverted repeats of mini-piggyBac may provide an ideal gene transfer vector that facilitates the introduction of an exogenous gene into the MSCs without altering (i.e., either enhance or inhibit) the global gene expression therein. On the contrary, the terminal inverted repeats of micro-piggyBac may be preferable for constructing gene transfer vector in mouse embryonic stem cells and human T cells.

In conclusion, the present disclosure provides a kit for selecting the most suitable piggyBac that possesses only the transposition activity in host cells without affecting the gene expression therein. Based on the selection result, a skilled artisan can construct a transposon that may efficiently introduce a gene of interest into the host cells without substantially altering or interfering (i.e., enhancing or suppressing) the global gene expression pattern in the host cells. Accordingly, the present disclosure provides a safe means to treat different diseases (e.g., a caner, an inflammatory disease, an immunodeficiency disease, an angiogenesis-associated disease, and a hormone-associated disease) via enabling a therapeutic gene to be appropriately and efficiently expressed in the subject in need thereof.

It will be understood that the above description of embodiments is given by way of example only and that various modifications may be made by those with ordinary skill in the art. The above specification, examples and data provide a complete description of the structure and use of exemplary embodiments of the invention. Although various embodiments of the invention have been described above with a certain degree of particularity, or with reference to one or more individual embodiments, those with ordinary skill in the art could make numerous alterations to the disclosed embodiments without departing from the spirit or scope of this invention.

What is claimed is:

1. A method of constructing a transposon capable of introducing an exogenous gene into host cells, comprising,
    (1) respectively transfecting the host cells with a control plasmid and a first to a fourth plasmids, wherein,
        the control plasmid consists essentially of, a gene cassette, which comprises a promoter of SEQ ID NO: 5 and a reporter gene operably linked to the promoter; and
        the first to the fourth plasmids consist essentially of, the gene cassette of the control plasmid and, respectively, a first to a fourth terminal repeats disposed upstream of the gene cassette, wherein the first to the fourth terminal repeats respectively consist of the nucleotide sequences of SEQ ID NOs: 1 to 4;
    (2) determining a control expression level of the reporter gene of the control plasmid in the host cells and respective expression levels of the respective reporter genes of the first to the fourth plasmids in the host cells; and
    (3) constructing the transposon that consists essentially of, (i) an expression cassette comprising a non-prokaryotic promoter and an exogenous gene operably linked to the non-prokaryotic promoter, (ii) a first selected terminal repeat, which is one of the first to the fourth terminal repeats that elicits an expression level closest to the control expression level, and (iii) a second selected terminal repeat, wherein,
        (3a) when the first selected terminal repeat is the first or the third terminal repeat, the first selected terminal repeat is disposed upstream of the expression cassette, and the second selected terminal repeat is the second or the fourth terminal repeat that is disposed downstream of the gene cassette; or
        (3b) when the first selected terminal repeat is the second or the fourth terminal repeat, the first selected terminal repeat is disposed downstream of the expression cassette, and the second selected terminal repeat is the first or the third terminal repeat that is disposed upstream of the gene cassette.

2. The method of claim 1, wherein
    in the step (3a), the second selected terminal repeat is the second or the fourth terminal repeat that elicits an expression level closer to the control expression level; or
    in the step (3b), the second selected terminal repeat is the first or the third terminal repeat that elicits an expression level closer to the control expression level.

3. The method of claim 1, wherein
    in the step (3a), when the first selected terminal repeat is the first terminal repeat, the second selected terminal repeat is the second terminal repeat; or when the first selected terminal repeat is the third terminal repeat, the second selected terminal repeat is the fourth terminal repeat; or
    in the step (3b), when the first selected terminal repeat is the second terminal repeat, the second selected terminal repeat is the first terminal repeat; or when the first selected terminal repeat is the fourth terminal repeat, the second selected terminal repeat is the third terminal repeat.

4. The method of claim 1, wherein the host cells are mammalian origin or insect origin.

5. The method of claim 4, wherein the host cells are immune cells selected from the group consisting of, T cells, B cells, natural killer cells, dendritic cells, macrophages, and mast cells.

6. The method of claim 4, wherein the host cells are stem cells derived from bone marrow, adipose tissue, peripheral blood, umbilical cord blood, or dental pulp.

7. The method of claim 4, wherein the host cells are epithelial cells.

8. The method of claim 1, wherein the non-prokaryotic promoter is an inducible promoter.

9. The method of claim 1, wherein the non-prokaryotic promoter is a constitutive promoter.

10. The method of claim 9, wherein the non-prokaryotic promoter is cytomegalovirus (CMV) promoter, rous sarcoma virus (RSV) promoter, simian virus (SV40) promoter, mouse mammary tumor virus (MMTV) promoter, phosphoglycerate kinase (PGK) promoter, chicken beta-active promoter, elongation factor 1-alpha (EF1-α) promoter, human H1 promoter, or U6 promoter.

11. A kit comprising,
 a control plasmid consisting essentially of, a gene cassette, which comprises a promoter of SEQ ID NO: 5 and a reporter gene operably linked to the promoter; and
 a first to a fourth plasmids consisting essentially of, the gene cassette and, respectively, a first to a fourth terminal repeats disposed upstream of the gene cassette, wherein the first to the fourth terminal repeats respectively consist of the nucleotide sequences of SEQ ID NOs: 1 to 4.

12. The kit of claim 11, wherein the reporter gene encodes a fluorescent protein or a luminescent protein.

* * * * *